United States Patent [19]
Holloway

[11] Patent Number: 5,110,439
[45] Date of Patent: May 5, 1992

[54] CAPILLARY GEL COLUMN WITH POLYORGANOSILOXANE COUPLING LAYER

[75] Inventor: Robert R. Holloway, Montara, Calif.

[73] Assignee: Hewlett-Packard Company, Palo Alto, Calif.

[21] Appl. No.: 752,709

[22] Filed: Aug. 30, 1991

[51] Int. Cl.$^5$ .................. G01N 27/26; B01D 57/02
[52] U.S. Cl. .................. 204/299 R; 204/182.8; 204/180.1
[58] Field of Search ............. 204/299 R, 180.1, 182.8

[56] References Cited

U.S. PATENT DOCUMENTS

| | | | |
|---|---|---|---|
| 4,865,706 | 9/1989 | Karger et al. | 204/299 R X |
| 4,865,707 | 9/1989 | Karger et al. | 204/299 R X |
| 4,997,537 | 3/1991 | Karger et al. | 204/299 R X |

OTHER PUBLICATIONS

R. Anderson, Barry Arkles, and G. L. Larson, "Silicon Compounds Register and Review," *Petrarch Systems Catalog* (Bristol, Pa., 1987), pp. 54 and 266. The pages do not mention use in an electrophoretic column.

*Primary Examiner*—John Niebling
*Assistant Examiner*—John S. Starsiak, Jr.

[57] ABSTRACT

A polyacrylamide gel electrophoresis column includes a fused-silica tube, a polyacrylamide gel matrix and a polydimethysiloxane layer radially between and covalently attached to both the tube and the gel matrix. The method for forming this column involves covalently binding polyorganosiloxane to the inner wall of the tube, covalently attaching organosilane termini to the organosiloxane layer, and polymerizing acrylamide so as to incorporate the organosilane termini into the resulting polyacrylamide gel matrix. Buffer ions are then drawn into the column under an electric field of about 1000 volts per centimeter, and, at the same time, different reaction product ions are removed. The polyorganosiloxane layer stretches as the polyacrylamide shrinks during polymerization so that the organosiloxane is at least twice as thick as it would be without the gel matrix attached. The process yields a gel matrix which is securely attached to the tube, void-free, and under minimal mechanical stress. As a result, the column can withstand relatively high-voltage pre-electrophoresis and electrophoresis procedures.

8 Claims, 3 Drawing Sheets

CAPILLARY GEL COLUMN WITH POLYORGANOSILOXANE COUPLING LAYER

BACKGROUND OF THE INVENTION

This invention relates to polymer chemistry and, more particularly, to a polyacrylamide gel electrophoresis column and a method of making the same. A major objective of the invention is to produce a column with a gel matrix that is void-free and that withstands the stress of high-voltage electrophoresis without rupture or displacement.

Polyacrylamide gel electrophoresis (PAGE) is a prominent methodology for analyzing protein mixtures. In a typical PAGE procedure, a sample protein mixture is introduced at one end of a capillary column, which can be a fused silica tube filled with a polyacrylamide gel matrix. The gel matrix has a lattice structure with pores that act as a molecular sieve, allowing small particles to pass easily, but imparting frictional drag to larger particles. Charged biomolecules migrate through the gel within the electric field at speeds inversely related to their molecular weight. The differential speeds cause mixture components to separate into bands that can be detected as they pass a detector to provide an analysis. Where it is desirable to isolate a protein, the voltage can turned off, and the gel can be removed from the tube and separated by band.

Polyacrylamide gels are three-dimensional synthetic vinyl polymers most commonly formed from low molecular weight acrylamide and bisacrylamide monomers, the latter serving as a cross linker. Due to the action of an initiator, the monomer units in solution chemically bond to form a polymer with gel properties. However, the volume occupied by the polymerized gel is less than that of the monomer solution. Acrylamide shrinks about 0.25 milliliter (ml) per gram upon polymerization. Accordingly, this shrinkage can pull the gel away from the inner wall of the tube leaving non-sieving channels. These non-sieving channels diminish the ability of the gel column to separate molecular components during electrophoresis. Moreover, the gel can actually slide out of the tube during electrophoresis, impairing the separation process.

To alleviate the problem of non-sieving channels near the wall of the tube, the inner walls of capillary tubes have been coated with silylating or silanizing reagents, generally short, rigid carbon chains with a vinyl double bond at the free terminus. The acrylamide monomers bond covalently to the coating material as polymerization takes place so that the polymerized gel is tightly attached to the tube. This attachment minimizes the formation of non-sieving channels near the tube wall. However, the shrinkage induces stresses in the gel matrix so that voids can occur in the interior of the gel. These voids constitute gel inhomogeneities which disturb separation of sample components during electrophoresis and degrade gel column performance. Additionally, under the stress from gel shrinkage, pore sizes of the lattice network can be non-uniform.

U.S. Pat. No. 4,810,456 to Bente and Myerson discloses a technique to reduce gel shrinkage by applying high pressure to the monomer solution during polymerization. This method is applied in conjunction with coatings that bind the gel matrix to the column wall. The technique attempts to reduce shrinkage defects by compressing the monomer solution to a volume close to that expected of the polymerized gel, in other words, by preshrinking. However, this technique does not completely eliminate performance problems of the gel. The gels seem to be weaker near the center and do not last as long as desired. Additionally, the technique requires high pressure equipment which is costly.

What is needed is an electrophoretic gel column that can withstand greater electric fields and maintain its integrity for a greater number of runs. As a corollary, a method of making such a column is required, and the method should be economical and result in a gel which is securely attached to a column wall and free of interior voids.

SUMMARY OF THE INVENTION

In accordance with the present invention, a PAGE column includes a radially intermediate organosiloxane "tether" layer covalently bound to both a glass capillary tube and a polyacrylamide gel matrix. The method of the present invention involves introducing an polyorganosiloxane solution that reacts with silanol groups on the inner tube wall to form covalent bonds between the organosiloxane and the wall. A vinyl coupling reagent is then introduced to covalently bond with free termini of the organosiloxane layer so that the free termini become vinyl groups. The coated tube is then filled with acrylamide prepolymer, preferably monomer, and a cross-linking reagent. During polymerization, the vinyl groups are incorporated into the gel matrix so that the gel matrix is covalently bound to the tube wall via unbroken chains of covalent bonds, predominantly Si—O bonds. The column is then brought into ionic equilibrium with two buffer reservoirs, one on each end of the gel column, by setting different electric potentials at the reservoirs so that the electric field along the column is at least 500 volts per centimeter.

Preferably, the glass tube is of fused silica. The organosiloxane solution can include silanol-terminated polydimethylsiloxane. The vinyl coupling reagent can include methacryloxypropyltrichlorosilane. The cross-linking reagent can be methylenebisacrylamide. The buffer can be an SDS-PAGE (sodium dodecyl sulfate polyacrylamide gel electrophoresis) buffer such as Tris-HCl.

In the resulting structure, the gel matrix is bound to the tube via the tether layer. Each tether is a silane-terminated polyorganosiloxane polymer segment. Each tether includes a polyorganosiloxane chain and an organosilane link. Each chain includes at least 1,000 but preferably about 20,000 polyorganosiloxane segments.

During polymerization, the polyacrylamide gel shrinks. The polyorganosiloxane chains stretch so that the organosiloxane layer thickens. At the end of polymerization, the polyorganosiloxane layer is at least twice as thick as it would be without the gel-induced stretch. However, since organosiloxane can stretch to about twelve times its unstretched length, relatively little mechanical stress is imposed.

Since the gel matrix is under little mechanical stress, it is more capable of withstanding high voltages (500 V to 4000 V) during pre-electrophoresis and electrophoresis. Higher voltages mean faster throughputs during column manufacture, during column preparation and during electrophoresis. The faster throughputs translate into cost and time savings. These and other features and advantages of the present invention are apparent from the description below with reference to the following drawings.

DESCRIPTION OF THE PREFERRED EMBODIMENTS

Figure 1:
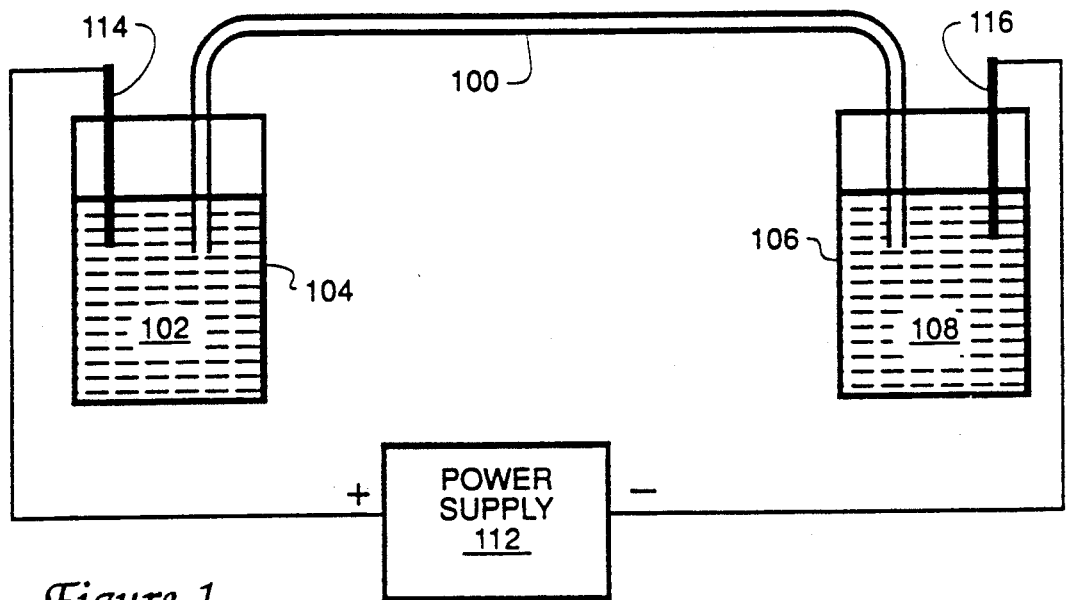
FIG. 1 is a schematic of an electrophoresis system incorporating a capillary column in accordance with the present invention.

A PAGE column 100 in accordance with the present invention is shown in FIG. 1 during a pre-electrophoresis procedure. One end of column 100 is disposed in a buffer solution 102 in a "positive" reservoir 104, while the other end of column 100 is disposed within a "negative" reservoir 106, also a containing a buffer solution 108. A power supply 112 charges a positive electrode 114 with respect to a negative electrode 116. Positive electrode 114 is disposed within positive reservoir 104 and negative electrode 116 is disposed within negative reservoir 106. During the procedure, power supply 112 provides an electrical potential of 15,000 volts total. This yields a field intensity of 1000 volts per centimeter, as column 100 is 15 centimeters long. Under the influence of the electric field, buffer ions from both reservoirs 104 and 106 migrate into column 100, purging column 100 of charged residues from the prior processing of column 100. This purging is preparatory to sample introduction and electrophoretic separation of the sample.

Figure 2:
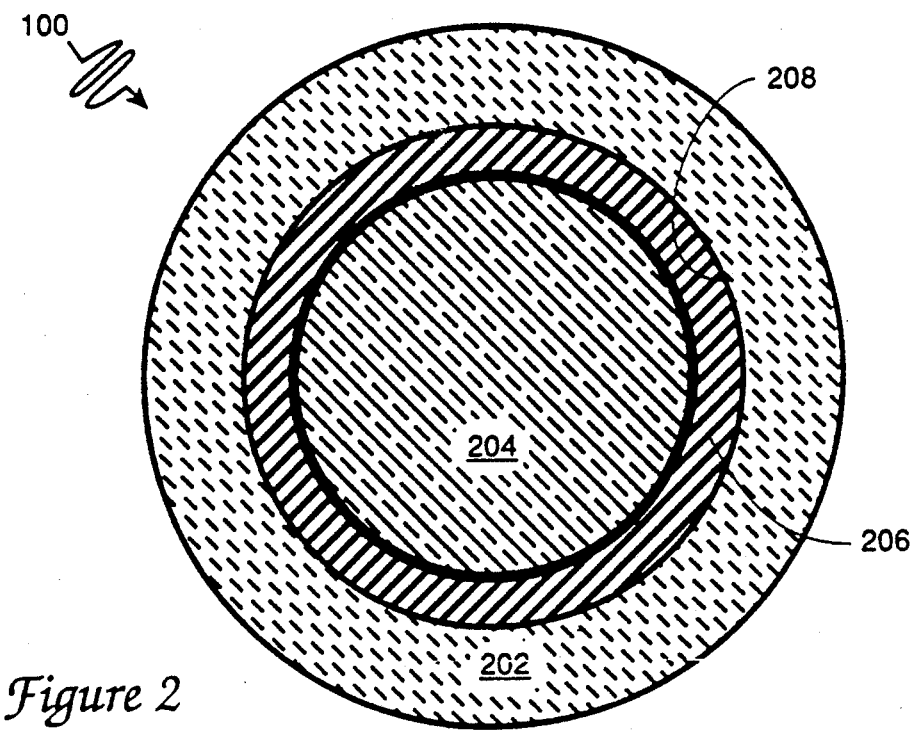
FIG. 2 is a schematic cross sectional view of the column of FIG. 1.

Column 100 comprises a fused silica tube 202 and a polyacrylamide gel 204 therewithin, as shown in FIG. 2. In accordance with the present invention, a polyorganosiloxane tether layer 206 is covalently attached to an inner wall 208 of tube 202 and to gel 204, thereby binding gel 204 within tube 202. Tether layer 206 provides an unbroken chain of covalent bonds between wall 208 and gel 204. Tether layer 206 is roughly a half micron thick in the radial dimension. Tension induced in tether layer 206 during polymerization causes the polyorganosiloxane polymer segments to stretch to at least twice their length at minimum energy. Thus, tether layer 206 is at least twice as thick as it would be in the absence of tension imposed by gel 204. Since the energy required to stretch organosiloxane the necessary amount is relatively low, the residual mechanical stresses on the gel are minimal. Minimizing gel stresses enhances gel integrity under high voltages and over more electrophoretic runs.

Figure 3:
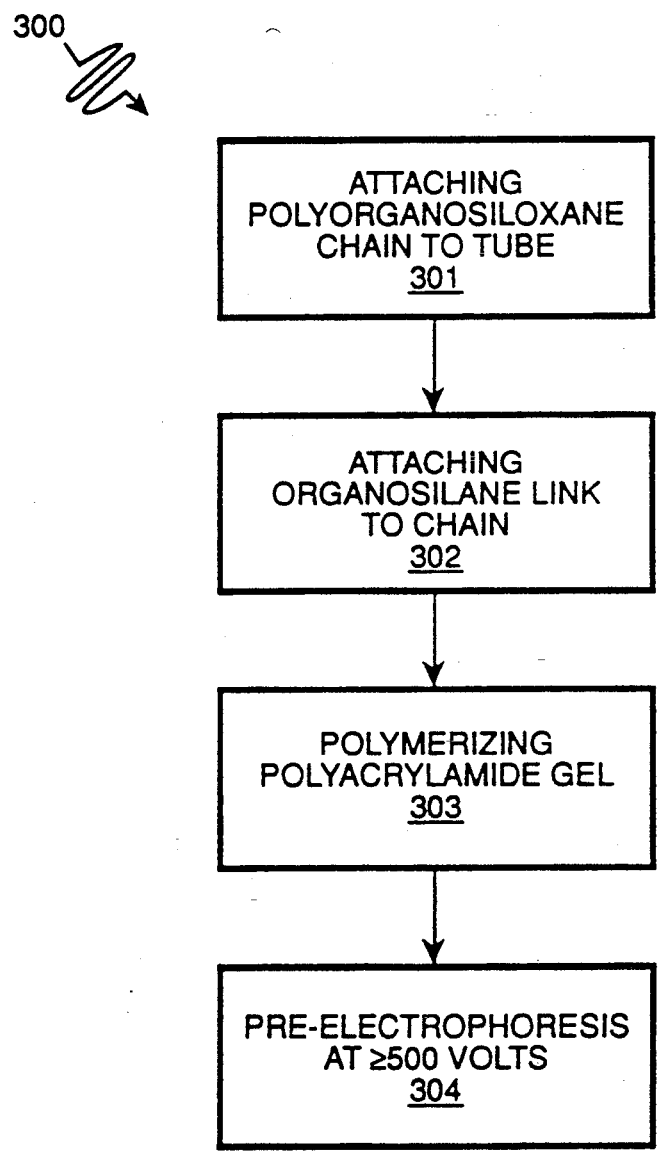
FIG. 3 is a flow chart of a method of the present invention employed to make the column of FIG. 1.

Column 100 is manufactured using a method 300 in accordance with the present invention and illustrated in FIG. 3. In a first step 301, a layer of polyorganosiloxane, specifically polydimethylsiloxane (PDS), is covalently attached to the inner wall of an appropriately prepared fused-silica capillary tube. In a second step 302, vinyl groups are covalently attached to the free termini of respective polyorganosiloxane molecules, resulting in vinyl-terminated PDS bound to the tube; the vinyl termini are to serve as links to bind the gel matrix.

In a third step 303, a prepolymer solution, including predominantly acrylamide monomer and a corresponding cross-linker, methylenebisacrylamide, is introduced into the tube and polymerized so that it covalently attaches to the functional reagent. During polymerization, the vinyl termini of the tether molecules are modified to be incorporated in the polymer chains of the gel matrix, which is thereby covalently attached to the polyorganosiloxane, and therethrough to the tube. In a fourth step 304, the tube is inserted into the configuration of FIG. 1; an electric field of about 1000 V/cm is applied to fill the column with buffer and to remove unwanted charged polymerization byproducts. Details of this method 300 are presented below.

The fused-silica capillary tube is fifteen centimeters long and 100 μm in diameter. The capillary tube is prepared by a three-minute flushing of its interior with an aqueous solution of 6M sodium hydroxide to maximize the presence of silanol (Si—O—H) structures at the inner wall. These silanol structures are the attachment sites for the organosiloxane.

Organosiloxane is attached by introducing a 5% by weight solution of silanol-terminated PDS (commercially available) in chloroform into the tube. The PDS have an average of about 20,000 dimethylsiloxy groups per molecule. Tetrabutyltitanate, at a concentration of 1% by weight of the PDS, is employed as a catalyst. The solution is forced into the tube and allowed to stand for about twelve hours to allow a PDS layer to form on the inner tube wall.

Figure 4:
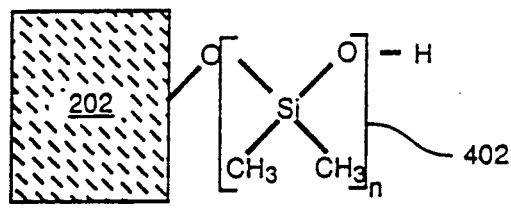
FIG. 4 is a schematic illustration of organosiloxane bound to a silica capillary tube, as provided by the first step of the method of FIG. 3.

In a predominant reaction, one silanol-terminated end of the PDS covalently binds to the tube wall to form a silyl-ether bond (Si—O—Si) via a condensation reaction with the hydroxyl groups on the silica; the other silanol-terminated end remains available for coupling to the gel through a coupling reagent. After this incubation, nitrogen is forced through the tube to remove the chloroform, leaving a polydimethylsiloxane chain 402 covalently bonded to tube 202, as shown in FIG. 4.

Figure 5:
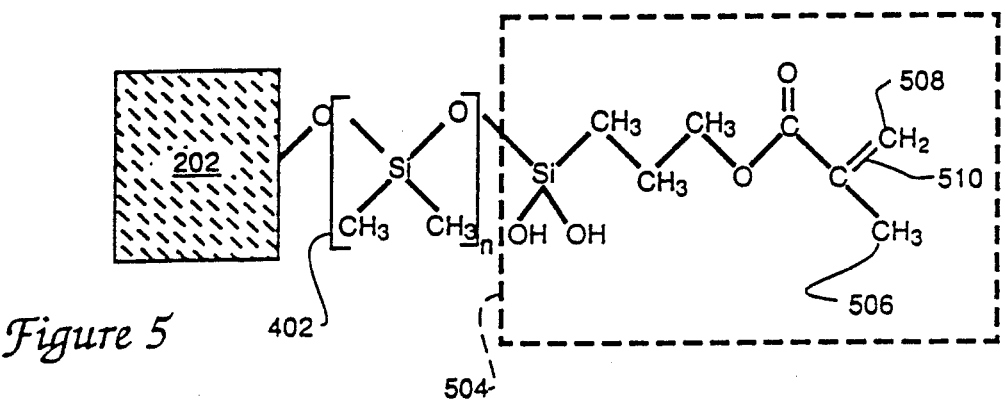
FIG. 5 is a schematic illustration of a molecular structure with a vinyl group covalently bound to the organosiloxane of FIG. 4 as provided by a second step of the method of FIG. 3.

Vinyl groups are attached by introducing a coupling reagent into the tube. A 2% solution of gamma-methacryloxypropyltrichlorosilane in toluene by volume is made to flow through the tube for fifteen minutes. This results in vinyl groups attaching to the free organosiloxane termini. A nitrogen flush is used to remove all liquid. This is followed by a one minute flush with water to leach out the HCl released when the methacryloxypropyltrichlorosilane binds to the organosiloxane via silyl-ether bonds. The resulting structure has a vinyl terminus 504 covalently attached to chain 402, as shown in FIG. 5. The vinyl terminus includes two carbon atoms 506 and 508 joined by a double bond 510.

Then the tube is filled with an aqueous solution of acrylamide monomer (10% by weight in solution), cross linker, free radical initiator, and buffer. The crosslinker is N, N'methylenebisacrylamide (3% in proportion to the acrylamide, 0.3% by weight in solution). The radical initiator is a combination of ammonium persulfate (0.1 mM in solution) plus an equal concentration of tetramethylethylenediamine (aka TMEDA or TEMED). The buffer is 50 mM sodium phosphate, pH 7.2 @ 25° C. Before the TEMED is added, the solution is degassed by bubbling helium through the solution.

Pressure is applied to force the monomer solution into the tube. The pressure driving the solution can be increased up to 20 bar as necessary to maintain flow into the tube. The pressure is required to counter the resistance that builds due to the viscosity of the polymerizing solution. This pressure helps prevent gas bubbles from developing in the gel. The pressure is maintained for 30 minutes, by which time polymerization is complete. Typically, the organosilane termini 504 of the tethers are incorporated into polyacrylamide polymer chains so that the resulting gel matrix is covalently bound to the tube via the tether layer.

Figure 6:
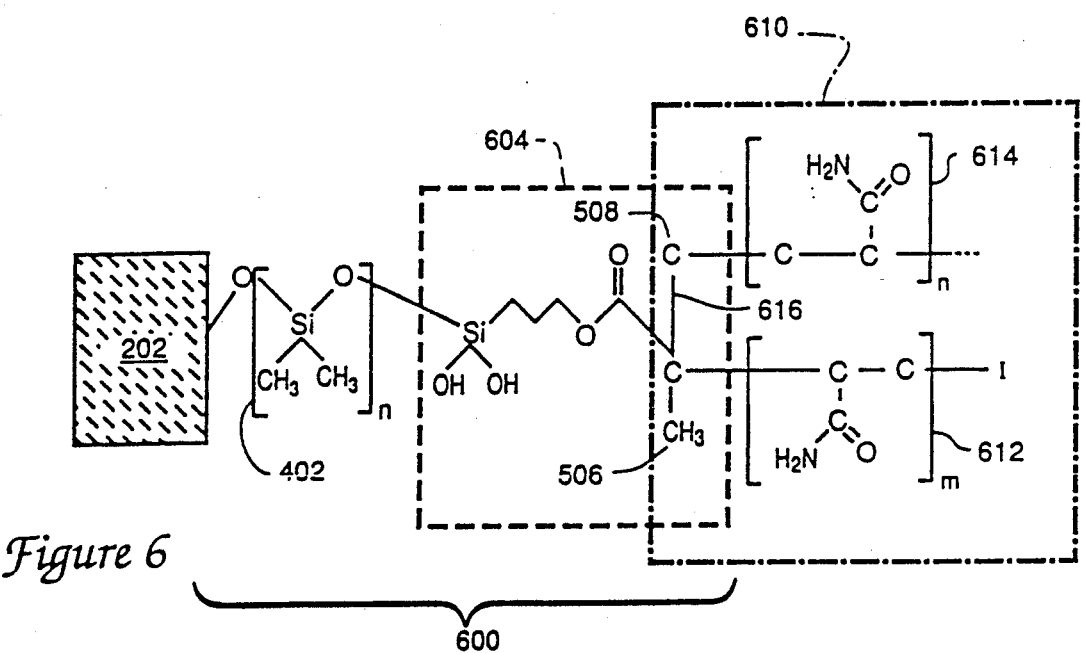
FIG. 6 is a schematic illustration of the molecular structure of the column illustrated in FIGS. 1 and 2 and as provided by a third step of the method of FIG. 3.

The structure upon polymerization includes the silica tube 202, a silane-terminated polyorganosiloxane tether polymer segment 600 and a polyacrylamide polymer chain 610, as shown in FIG. 6. Polyacrylamide polymer chain 610 is part of gel 204. Silane terminus 604 is incorporated into polyacrylamide gel 204, as indicated by the overlapping of link 604 and polyacrylamide chain 610 in FIG. 6. Tether 600 includes polydimethylorganosiloxane chain 402 with about 20,000 Si—O bonds and an organosilane link 604.

Gel 204 is represented by a single polyacrylamide chain 610; those skilled in the art recognize that there are many such chains and the chains are interconnected due to the action of the cross-linking reagent. Polyacrylamide chain 610 includes an initiator residue I, a first polyacrylamide segment 612 with m units, and a second polyacrylamide segment 614 with n units. Second polyacrylamide segment 614 is shown extending to a series of dots which represent the various ways in which such chains are known to continue and finally terminate in a polyacrylamide gel. During polymerization, the double bond 510 of FIG. 5 is replaced by a single bond 616, permitting polyacrylamide segment 612 to bond to carbon atom 506, while carbon atom 508 then serves as a site for growing second polyacrylamide segment 614.

Once polymerization is complete, both ends of tube 202 are inserted in electrophoresis buffer reservoirs 104 and 106, as shown in FIG. 1. The preferred SDS-PAGE buffer is 100 mM Tris-HCl, pK 8.4; "Tris" is tris(hydroxymethyl)aminomethane. A voltage of 15 kilovolts is applied across the column, which is 15 cm long, so that the field strength is 1000 volts per centimeter. The field is maintained for 15 minutes as buffer ions replace other mobile ions along the column. The pre-electrophoresis step causes the buffer ions to replace potentially deleterious charged products of the polymerization reaction. The resulting structure is column 100 as shown in cross-section in FIG. 2.

The gel maintains its integrity in the presence of repeated applications of strong fields since it is bound to the wall, yet free of voids and subject to minimal internal stress. Subsequent pre-electrophoresis and electrophoresis procedures can also be conducted with field strengths above 500 V/cm, to maintain a high column throughput.

While the foregoing has described the salient features of the preferred method and structure, those skilled in the art can recognize that some variations are inherently encompassed. For example, some PDS molecules attach to other PDS molecules, so that they do not provide a terminus for the gel. In some case, the gel matrix may attach to intermediate sites along a PDS molecule. Further, while the foregoing structure and method represent preferred embodiments, the present invention provides for a range of alternatives, some of which are indicated below.

Different capillary tubes are provided for. Fused silica is the preferred material, however, many alternative silica-based glasses can be used. Dimensions can be varied. The inner diameter can vary from $5\mu$ to $500\mu$. The tube need not be circular in cross section, but may as well be rectangular or elliptical. The length can vary from 5 cm to 200 cm. It is not necessary that the material or dimensions be uniform over the length of the capillary tube. The length of a capillary tube need not be the same at the beginning of the inventive method as it is at the end. For example, a relatively long gel-filled capillary tube can be spliced to yield one or more capillaries columns of a desired length.

Different procedures for activating the tube surface are provided for. Other caustic aqueous solutions can be used to maximize silanol sites. Alternatively, a strong mineral acid, such as sulfuric acid ($H_2SO_4$) or nitric acid ($HNO_3$) can be used. In some cases, a sufficient number of sites may be present without a special activating procedure.

Different organosiloxane solutions are provided for. A tin soap, dibutyltin dilaurate, can be used as a catalyst for silanization instead of the tetrabutyltitanate. Different termini are provided for. For example, a chlorodimethylsiloxy-terminated PDS can be used. Chlorodimethylsiloxy-terminated PDS can be prepared from commercially available silanol-terminated PDS by substituting chlorine for the hydroxyl groups on the end. The solution is made to flow through the capillary tube, whereby, in a predominant reaction, a chlorodimethylsiloxy terminus at one end of an organosiloxane molecule reacts with a surface-bound silanol group to form surface-bound PDS with a chlorodimethylsiloxy group available at its free end. The reaction results in HCl byproduct. The bound organosiloxane layer is washed with water to substitute a hydroxyl group for the chlorine at the free terminus and to remove HCl. A similar procedure can be used to bind a trichlorosilyloxy-terminated polydimethylsiloxane. This material provides two additional hydroxyl groups for binding a gel, but is more difficult to synthesize.

The coupling reagent can take different forms. For example, the preferred methacryloxypropyltrichlorosilane can be dissolved in xylene instead of the preferred toluene. Acryloxypropyltrichlorosilane is an alternative chlorine-bearing coupling reagent. Alternatively, alkoxy reagents such as methacryloxypropyltrimethoxysilane, or methacryloxypropyltriethoxysilane, or other trialkoxysilane, can be used although the resulting reactions are more time consuming and require heating.

The alkoxy coupling reagents can be dissolved 2% by volume in a mixture of 90% water, 9.9% ethanol, with about 0.1% acetic acid. In solution, the trialkoxysilane is hydrolyzed to form a trihydroxysilane. This solution is made to flow through the tube for three minutes. When this molecule is introduced to the attached PDS, a condensation reaction covalently binds the trihydroxysilane to the PDS at the terminal hydroxyl group. A catalyst such as tetrabutyltitanate may be added in this step to assure a timely reaction. Alternatively, dibutyltin dilaurate can be used as a catalyst. Then the tube is flushed with ethyl alcohol for one minute to remove the acetic acid. A 10-second nitrogen flush is followed by baking at 100° C. for 10 minutes; it is thought that this heating removes water, thereby converting a hydrogen bond to silyl-ether bond. This silyl-ether bond leaves vinyl monomer groups at the free ends of the organosiloxane tether molecules.

Different gel formulations, cross-linkers, and catalysts are provided for. For example, stannous octoate can be used as the catalyst for the gel matrix. Different buffers can also be used. For example, Tris-borate and Tris-glycine can be used as SDS buffers. Detergents other than SDS can be used, and the choice of detergent can affect the selection of buffer. Where the analytes, for example, nucleic acids, are not complex proteins, detergents need not be included with the buffer, and the selection of buffer can be made accordingly.

While the steps of the invention have been presented in their preferred order, the chronology of steps is not fixed. The vinyl groups can be attached to the organosiloxane before the organosiloxane is attached to the capillary. In other words, steps 301 and 302 can occur in the reverse order. For example, vinyl can be attached at both ends, and one vinyl group removed later. Alternatively, one organosiloxane terminus can be blocked, allowing vinyl to attach to only one end. These and other variations upon and modifications to the described embodiments are provided for by the present invention, the scope of which is limited only by the following claims.

What is claimed is:

1. A capillary column for polyacrylamide gel electrophoresis, said column comprising:
   a glass capillary tube having an inner wall;
   a polyacrylamide gel matrix within said tube; and
   a polyorganosiloxane layer radially between said inner wall and said matrix, said polyorganosiloxane layer being covalently bound to said inner wall and to said gel matrix so that said gel matrix is attached to said tube via unbroken series of covalent bonds, each of said series including in excess of 1000 Si—O bonds.

2. A column as recited in claim 1 wherein said polyorganosiloxane layer is under tension imposed by said inner wall and said gel matrix so that its radial thickness is at least twice what it would be in the absence of said gel matrix.

3. A column as recited in claim 1 wherein said organosilane layer includes organosilane-terminated polyorganosiloxane polymer segments, said segments having organosilane termini covalently bound to said gel matrix.

4. A method of preparing a column for polyacrylamide gel electrophoresis, said method comprising the steps of:
   covalently attaching a layer of organosiloxane to the inner surface of a glass capillary tube;
   covalently attaching organosilane termini to said organosiloxane;
   filling said tube with acrylamide prepolymer and cross-linking reagent and initiating polymerization so that the resulting polyacrylamide gel matrix incorporates said organosilane termini; and
   incorporating buffer ions into said matrix by applying an electric field along the length of said glass capillary tube, said field have a field to strength of at least 500 volts per centimeter.

5. A method as recited in claim 4 wherein said step of covalently attaching organosilane termini to said organosiloxane occurs before said step of covalently attaching said layer of organosiloxane to said inner surface.

6. A method as recited in claim 4 wherein said step of covalently attaching organosilane termini to said organosiloxane occurs after said step of covalently attaching said layer of organosiloxane to said inner surface.

7. A method as recited in claim 4 wherein said organosiloxane is a polydimethylsiloxane.

8. A method as recited in claim 5 wherein said glass is fused silica, said organosilane is gamma-methacryloxypropyltrichlorosilane, and said cross-linking reagent is methylenebisacrylamide.

* * * * *